(12) United States Patent
Harris et al.

(10) Patent No.: US 7,790,391 B2
(45) Date of Patent: Sep. 7, 2010

(54) METHODS OF EQUALIZING REPRESENTATION LEVELS OF NUCLEIC ACID TARGETS

(75) Inventors: Timothy D. Harris, Toms River, NJ (US); John J. Boyce, IV, Bridgewater, MA (US)

(73) Assignee: Helicos Biosciences Corporation, Cambridge, MA (US)

( * ) Notice: Subject to any disclaimer, the term of this patent is extended or adjusted under 35 U.S.C. 154(b) by 54 days.

(21) Appl. No.: 12/058,032

(22) Filed: Mar. 28, 2008

(65) Prior Publication Data

US 2009/0246760 A1    Oct. 1, 2009

(51) Int. Cl.
*C12Q 1/68* (2006.01)
(52) U.S. Cl. .................... 435/6; 435/91.1; 435/91.2; 536/23.1; 536/22.1
(58) Field of Classification Search ............. None
See application file for complete search history.

(56) References Cited

OTHER PUBLICATIONS

Dahl et al. PNAS vol. 104:9387-9392. 2007.*

* cited by examiner

*Primary Examiner*—Heather Calamita
(74) *Attorney, Agent, or Firm*—Thomas Meyers; Adam Schoen; Brown Rudnick LLP

(57) ABSTRACT

The disclosure provides methods of reducing the range of representation levels of nucleic acid targets. The methods are particularly useful for multi-target analyses benefiting from a low variance of target representations, such as, e.g., single molecule sequencing and/or heterozygous genotyping, and pathogen diagnosis. Two general methods are provided. In Method 1, starting concentrations of probes are adjusted. In Method 2, target-specific probes are "binned," i.e., several subsets of probes are selected based on similar representation levels. Thereafter, each subset of corresponding targets is extracted, with or without amplification, using a separate portion of the sample (i.e., separate vessels).

25 Claims, 3 Drawing Sheets

METHODS OF EQUALIZING REPRESENTATION LEVELS OF NUCLEIC ACID TARGETS

TECHNICAL FIELD

The invention is in the field of molecular biology and relates to methods for nucleic acid analysis. In particular, the invention relates to methods for equalizing nucleic acid target representation yields in probe-specific extraction of targets.

BACKGROUND

Many types of studies require analysis of a large number of genomic regions, with as many as 200,000 target regions analyzed. Normally, each target region is amplified in a separate reaction in an individual sample. The sample requirements and expense of so many separate reactions makes studies with large numbers of genomic targets prohibitive. The complete analysis of complex multi-component systems is frequently beyond the capability of existing methods. Simplification of the system, i.e., selection of the key components and discarding others, allows a useful study to be designed.

In the case of nucleic acid sequencing, isolation of the target sequence is frequently realized by amplification (e.g., by PCR). One solution is to combine the multiple amplification and isolation reactions into a single vessel, i.e., multiplexing. However, two problems arise. First, for PCR, the interaction between the probes generates large numbers of spurious products if multiple probes are combined. Even if this problem is solved, the efficiency of isolation is not uniform, resulting in a large range of concentrations for the selected targets. This concentration range then requires a large dynamic range of sensitivity for the subsequent analysis. For example, a typical DNA chip has a useful sensitivity range of ~30×. If the PCR amplicon mixture is probed with such a DNA chip, all amplicons below the 30× range could not be detected. Targeted gene sequencing presents a similar problem. A single gene is about 1 part in $10^5$ of a whole human genome, while the exons in one gene are about 2 parts in $10^6$ of a whole genome. Thus, a typical targeted gene study involving 10-500 genes would require the extraction of 100-5000 separate gene fragments per sample. Furthermore, a genomic sample of 3 µg of human DNA contains about $10^6$ copies of the genome, and the range of isolated genes would vary in copy number by 100-1000×. Additionally, some applications, such as heterogyzous genotyping, may require read depths of 20× or more, which translates the whole sample being sequenced to a depth of ~20,000×, making the cost of the data very high. If all fragments could be extracted in one or a few reactions (i.e., multiplexed) much less sample would be required, resulting in lower reagent consumption and labor costs. However, none of the available mutiplexing methods provide uniform efficiency.

Accordingly, there is a need for methods for isolation of multiple genes with substantially similar representation levels.

SUMMARY OF THE INVENTION

Simultaneous probe-specific extraction of multiple nucleic acid targets typically yields a wide range of target representations in the final sample. Multiple factors contribute to this variance, both at the target capture stage as well as during amplification of targets. The invention provides methods of equalizing the variation in nucleic acid target representations in the final sample containing the extracted targets (amplified or non-amplified). Using methods of the invention, the targets' range of representation levels for a given set of probes/targets is generally reduced relative to the range obtained otherwise. The methods described here are particularly useful for those types of multi-target analysis that benefit from lower variance of target representations, such as, for example, single molecule sequencing, heterozygous genotyping, and pathogen diagnostics.

An initial range of representation levels is first determined for a given set of probes/targets. To that end, a plurality of selective probes is contacted with a sample containing targets, and all probe-specific targets are extracted together. In some embodiments, a multiplex amplification of targets is also performed. These extracted, and optionally amplified, targets form the initial range of representation levels.

The invention provides two general methods (Method 1 and Method 2) that reduce the target representation variance in the analytic sample.

In Method 1, the starting concentrations of probes are adjusted up or down based on their initial representation levels. For example, the starting concentrations of the probes yielding lower representation levels are increased, while the starting concentrations of the probes yielding higher representation levels are reduced.

In Method 2, the probes are "binned," i.e., several subsets of probes are selected based on similar representation levels. For example, probes with low, medium, and high representation levels may be grouped, respectively, into three subsets. Thereafter, each subset of corresponding targets is extracted, with or without amplification, using a separate portion of the sample (i.e., separate vessels). For subsequent analysis, the resulting targets may be combined into a single sample in proportions adjusted so that a reduced range is maintained. For example, a larger portion of the low-representation subset is combined with a smaller portion of high-representation subset. In some embodiments of Method 2, multiplex amplification of targets with binned probes is performed in separate portions of the sample, thereupon, the separate reactions are combined.

In some embodiments, the targets are captured by circularizing probes annealed to their respective targets and removing non-circularized nucleic acids prior to the target isolation.

In some embodiments, targets are analyzed by sequencing, e.g., sequencing by synthesis. In preferred embodiments, the sequencing is performed at a single molecule resolution, e.g., with the targets immobilized on a support.

Additional aspects of the invention are described in detail below.

DETAILED DESCRIPTION OF THE INVENTION

Figure 1:
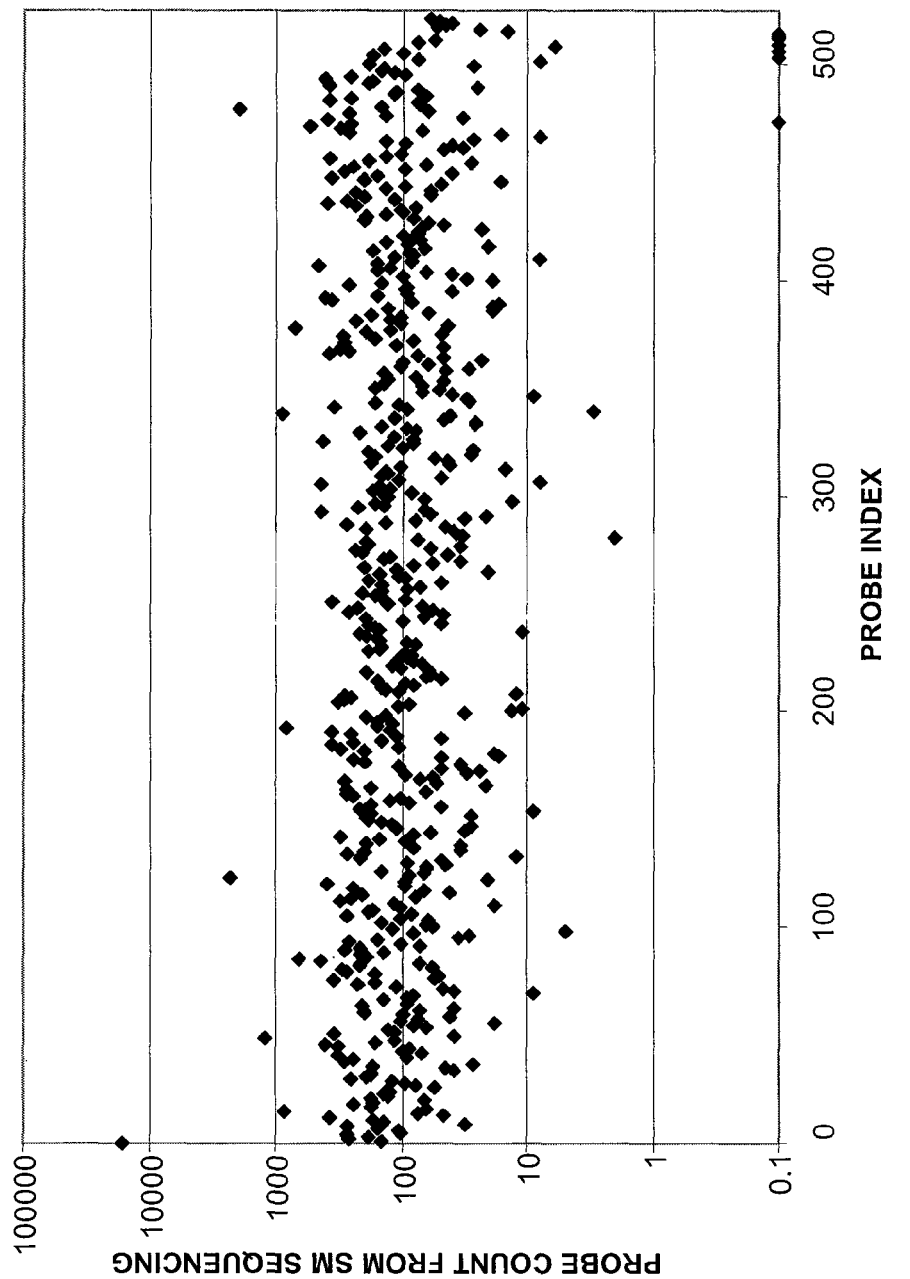
FIG. 1 provides results of the study described in the Example. The diagram shows the number of amplicons detected vs. probe identity as numbered from 1 to 518.

The invention provides methods for reducing the range of representation levels of nucleic acid targets in biological samples. According to the methods, the range of target representation levels for a given set of targets/probes is reduced, generally, relative to that obtained without such methods. The targets may be captured and analyzed directly, or they may be amplified, for example, by multiplex PCR amplification (amplification of two or more target sequences in the same reaction).

In general, an initial range of representation levels is first determined for a given set of probes/targets. To that end, a plurality of selective probes is contacted with a sample containing targets, and all probe-specific targets are extracted together. In some embodiments, a multiplex amplification of targets is performed. These extracted and optionally amplified targets form the initial range of representation levels.

The range of representation levels typically is either the difference or the ratio of the two parameters: 1) the abundance of the most represented target and 2) the copy number of the least represented target in the sample. (Outliers are generally excluded, but need not be in some implementations.) The abundance of a target may be determined or expressed indirectly as $C_t$, mass, copy number, a number or the percentage of sample fractions containing a target, etc. The representation range can be determined by any suitable method. The initial representation range will vary depending on the nature of the biological sample, the specificity of the probes, the initial concentration of each target in the sample, the initial concentration of the probes, efficiency of the amplification process and other factors. In some embodiments, the initial range of representation levels is at least 100×, for example, 200×, 500×, 1,000×, 10,000× or higher.

The invention provides at least two methods (generally referred to as "Method 1" and "Method 2") to reduce target representation variance in the final sample. The methods can be used individually or in combination with each other.

Method 1—In Method 1, starting concentrations of probes are adjusted. The starting concentrations of the probes yielding lower representation levels are increased, while the starting concentrations of the probes yielding higher representation levels are reduced. Generally, Method 1 comprises the following steps:

a) contacting a plurality of probes with a sample comprising a plurality of targets;
b) capturing the plurality of nucleic acid targets with the plurality of probes;
c) optionally, amplifying the captured targets using the plurality of probes;
d) determining an initial range of representation levels of the captured nucleic acid targets;
e) repeating steps a), b), and c) (if the latter is performed), at starting concentrations of the probes adjusted to reduce the range of representation levels of captured targets relative to the initial range, thereby producing a final sample.

In some embodiments, the starting concentrations of at least 5, 10, 50, 100 probes are adjusted at least 2-, 3-, 4-, 5-, 10-fold or more up or down. In some embodiments, the probes are divided into 2, 3, 4, 5, 10, or more subsets according to the similarity of their representation levels, and the starting concentration of the entire subset is thus adjusted.

Method 2—In Method 2, the probes are "binned," i.e., several subsets of probes are selected based on similar representation levels. Then, each subset of corresponding targets are extracted individually (with or without amplification) using a separate portion of the sample (the procedure generally referred to as "binning"). The resulting isolated targets may then be combined into a single sample at various proportions so as to maintain a reduced range of target representation levels. Generally, Method 2 comprises the following steps:

a) contacting a plurality of probes with a sample comprising a plurality of targets;
b) capturing the plurality of nucleic acid targets with the plurality of probes;
c) optionally, amplifying the captured targets using the plurality of probes;
d) determining an initial range of representation levels of the captured nucleic acid targets;
e) selecting two or more subsets of targets/probes so that each of the subsets contains targets of a range of representation levels which is reduced relative to the initial range; and
f) repeating steps a), b), and c) (if the latter is performed), using separate samples so that each sample contains only targets/probes of different selected subsets.

In some embodiments, the Method 2 further comprises:
g) combining the samples produced in step f) or portions thereof to produce a final sample.

In both Method 1 and Method 2, the range of representation is reduced in the final sample relative to the initial range. In some embodiments, the reduced range in the final sample (e.g., before analysis) is less than 50×, 30×, 20×, 10×, 5×, 3×, 2× or lower. Accordingly, in some embodiments, the range of representation levels is reduced by at least 2-, 5-, 10-, 50-, 100-, 500-, 1,000-fold or more.

Multiplex amplification—In some embodiments, the targets are amplified in a multiplex fashion prior to analysis. Target sequences are typically amplified using respective sequence-specific probes. As many as hundreds or a greater number of targets may be amplified in the same reaction. Most commonly, multiplex amplification of nucleic acids is performed using the polymerase chain reaction (PCR), however, the invention may also be used with other amplification techniques amenable to multiplexing, including the ligase chain reaction (LCR), the transcription-based amplification system (TAS), the nucleic acid sequence-based amplification (NASBA), the strand displacement amplification (SDA), rolling circle amplification (RCA), hyper-branched RCA (HRCA), etc. Numerous target-specific probes are available from commercial sources. A desired set of probes can also be synthetically made using conventional nucleic acid synthesis techniques. For example, probes may be synthesized on an automated DNA synthesizer using standard chemistries, such as, e.g., phosphoramidite chemistry. In the methods of the invention, a plurality of target-specific probes may comprise two or more probes specific to different targets, e.g., 3, 4, 5, 10, 50, 100, 200, 300, 500, 1,000, 10,000 or more. All or some of the probes will have corresponding targets in a given sample. Thus, a multiplex amplification reaction may be performed on two or more targets, e.g., 3, 4, 5, 10, 50, 100, 200, 300, 500, 1,000, 10,000 or more.

Circularization—In some embodiments of Methods 1 and 2, the method further includes circularizing probes annealed to respective targets. Following the circularization of the target, the linear (non-target) nucleic acids are removed from the sample. Next, the circularized target/probe is linearized and the target is bound to a support for further analysis. Circular constructs for PCR-based amplification have been previously described (see, e.g., PCT Application Publication No. WO 2005/111236). Circularization of nucleic acids has been previously used to increase efficiency of PCR-based amplification of nucleic acids (see, e.g., Dahl et al. (2005) Nucleic Acid Res., 33, e71; and Dahl et al. (2007) Proc. Natl. Acad. Sci., 104:9387-9392). Circularization of targets/probes in the context of sequencing is described in, e.g., U.S. patent application Ser. No. 11/958,173. In general, a probe used for circularization comprises: 1) a double-stranded nucleic acid having two overhang ends that are specific (i.e., complementary) to two sites of the target nucleic acid, 2) one or more cleavage site(s) in the double-stranded region of the probe, and 3) other optional elements. Accordingly, prior to the amplification, Methods 1 or 2 may include ligating the probes and the targets to form closed circular nucleic acids and removing non-circularized linear nucleic acids (e.g., by exonuclease treatment).

Nucleic Acid Targets

Target nucleic acids may come from a variety of sources. For example, nucleic acids may be naturally occurring DNA or RNA (e.g., mRNA or non-coding RNA) isolated from any source, recombinant molecules, cDNA, or synthetic analogs. For example, the target nucleic acid may include whole genes, gene fragments, exons, introns, regulatory elements (such as promoters, enhancers, initiation and termination regions, expression regulatory factors, expression controls, and other control regions), DNA comprising one or more single-nucleotide polymorphisms (SNPs), allelic variants, and other mutations. The target nucleic acid may also be tRNA, rRNA, ribozymes, splice variants, antisense RNA, or siRNA.

Target nucleic acids may be obtained from whole organisms, organs, tissues, or cells from different stages of development, differentiation, or disease state, and from different species (human and non-human, including bacteria and virus). Various methods for extraction of nucleic acids from biological samples are known (see, e.g., Nucleic Acids Isolation Methods, Bowein (ed.), American Scientific Publishers, 2002). Typically, genomic DNA is obtained from nuclear extracts that are subjected to mechanical shearing to generate random long fragments. For example, genomic DNA may be extracted from tissue or cells using a Qiagen DNeasy Blood & Tissue Kit following the manufacturer's protocols.

The length of the target nucleic acid may vary. The average length of the target nucleic acid may be, for example, at least 300, 350, 400, 450, 500, 550, 600, 700, 800, 900, 1000, 2000, 3000, 4000, 5000 nts or longer. In some embodiments, the length of the target is between 300 and 5000 nts, 400 and 4000 nts, or 500 and 3000 nts.

Analysis Methods, Including Sequencing

In both Method 1 and Method 2, the final sample may be subjected to additional manipulations, and if desired, analyzed by any suitable method, e.g., sequencing, for example, for exonic re-sequencing, genotyping, single nucleotide polymorphism (SNP) detection) or used for allele quantification, pathogen diagnostics, etc. Methods of the invention are particularly useful for those types of nucleic acid analysis that benefit from a low variance of target representations. The invention can be used with any suitable analysis method, including sequencing, detection with hybridization probes, etc.

In preferred embodiments, the nucleic acid targets are analyzed by sequencing by synthesis. For example, in single-molecule sequencing, it may be advantageous to reduce the variance so that the required sequencing depth (also referred to as "sequence coverage") is reduced. This requirement generally is a function of the importance of achieving a high probability that each base in a sequence will be measured, and measured accurately within acceptable error tolerances. Error tolerances, and even the need to measure each base, may vary depending on the purpose of the experiment. Accordingly, in some embodiments, the sequencing applications include sequencing by synthesis with sequence coverage being above 1×, 2×, 3×, 5×, 10×, 20× or higher. For example, for a given set of targets with a total length of 1,000,000 bases, 1× coverage means that 1,000,000 bases are sequenced, some of which may be multiples of the same sequence.

Any suitable sequencing method may be used, including Sanger sequencing. For example, the following sequencing platforms are currently available: the Genome Sequencers from Roche/454 Life Sciences, the 1G Analyzer from Illumina/Solexa, and the Heliscope system from Helicos Biosciences. Two sequencing-by-ligation platforms are also currently available: the SOLiD system from Applied BioSystems and the Polonator G.007 from Danaher Motion. Additional sequencing platforms have also been described by Pacific BioSciences and VisiGen Biotechnologies. Each of these platforms can be used in the methods of the invention. In some embodiments, the sequencing platforms used in the methods of the present invention have one or more of the following features:

1) four differently optically labeled nucleotides are utilized (e.g., 1G Analyzer, Pacific BioSciences, and Visigen);
2) sequencing by ligation is utilized (e.g., SOLiD, Polonator);
3) pyrophosphate detection is utilized (e.g., Roche/454);
4) four identically optically labeled nucleotides are utilized (e.g., Helicos);
5) fluorescent energy transfer (FRET) is utilized (e.g., Visigen).

In some embodiments, a plurality of nucleic acid molecules being sequenced is bound to a support. To immobilize the nucleic acid on a support, a capture sequence/universal priming site can be added at the 3' and/or 5' end of the template. The nucleic acids may be bound to the solid support by hybridizing the capture sequence to a complementary sequence covalently attached to the solid support. The capture sequence (also referred to as a universal capture sequence) is a nucleic acid sequence complementary to a sequence attached to a solid support that may dually serve as a universal primer. In some embodiments, the capture sequence is polyN$_n$, wherein N is U, A, T, G, or C, n≧5, e.g., 20-70, 40-60, e.g., about 50. For example, the capture sequence could be polyT$_{40-50}$ or its complement.

As an alternative to a capture sequence, a member of a coupling pair (such as, e.g., antibody/antigen, receptor/ligand, or the avidin-biotin pair as described in, e.g., US Pat. App. Pub. No. 2006/0252077) may be linked to each fragment to be captured on a surface coated with a respective second member of that coupling pair.

The solid support may be, for example, a glass surface such as described in, e.g., US Pat. App. Pub. No. 2007/0070349. The surface may be coated with an epoxide, polyelectrolyte multilayer, or other coating suitable to bind nucleic acids. In preferred embodiments, the surface is coated with epoxide and a complement of the capture sequence is attached via an amine linkage. The surface may be derivatized with avidin or streptavidin, which can be used to attach to a biotin-bearing target nucleic acid. Alternatively, other coupling pairs, such as antigen/antibody or receptor/ligand pairs, may be used. The surface may be passivated in order to reduce background. Passivation of the epoxide surface can be accomplished by exposing the surface to a molecule that attaches to the open epoxide ring, e.g., amines, phosphates, and detergents.

Subsequent to the capture, the sequence may be analyzed, for example, by single molecule detection/sequencing, e.g., as described in the Example and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or can be done in a step-and-repeat mode. For real-time analysis, different optical labels to each nucleotide may be incorporated and multiple lasers may be utilized for stimulation of incorporated nucleotides.

The following Example provides illustrative embodiments of the invention and does not in any way limit the invention.

EXAMPLE

Equalization of a 518-Probe Set

Tags are prepared as described through step C in FIG. 1 of Dahl et al. (2007) PNAS, 104:938, from a pool of 518 probes, except that the probe concentrations were adjusted up or down up to 10× from the former concentration according to the relative representation found in Dahl. The sample was then a multiplex pool of 518 PCR amplicons with variable representation. The entire probe pool is then subjected to a polyA tailing process substantially as described in US Pat. App. Pub. No. 2007/0070349. On average, 25 A bases were added to each amplicon in the pool followed by a ddA-Cy3 to terminate and label the amplicon. These polyA-tailed amplicons were then captured onto a sequencing surface specially prepared for this test. The surface bound capture consisted of the PCR primer complement and by dT20 with the dA20 nearest the surface. In this way, 38 bases of single-stranded sequence, complementary to the 3' end of each amplicon, was available on the surface to both capture the amplicons by hybridization and act as a sequencing-by-synthesis primer. Since all the amplicons are still whole, only the first 20-30 bases will be read. However, this is more than sufficient to "count" representation of the extracted tags. The sample is sequenced, one pass sequencing up substantially as described in US Pat. App. Pub. No. 2007/0070349. The sequences are aligned against a dictionary of words 50 bases long derived from the known target sequences of the probes. The first 20 bases of each word are the same as the probe sequences. In this way, a count of each probe can be made.

Figure 2:
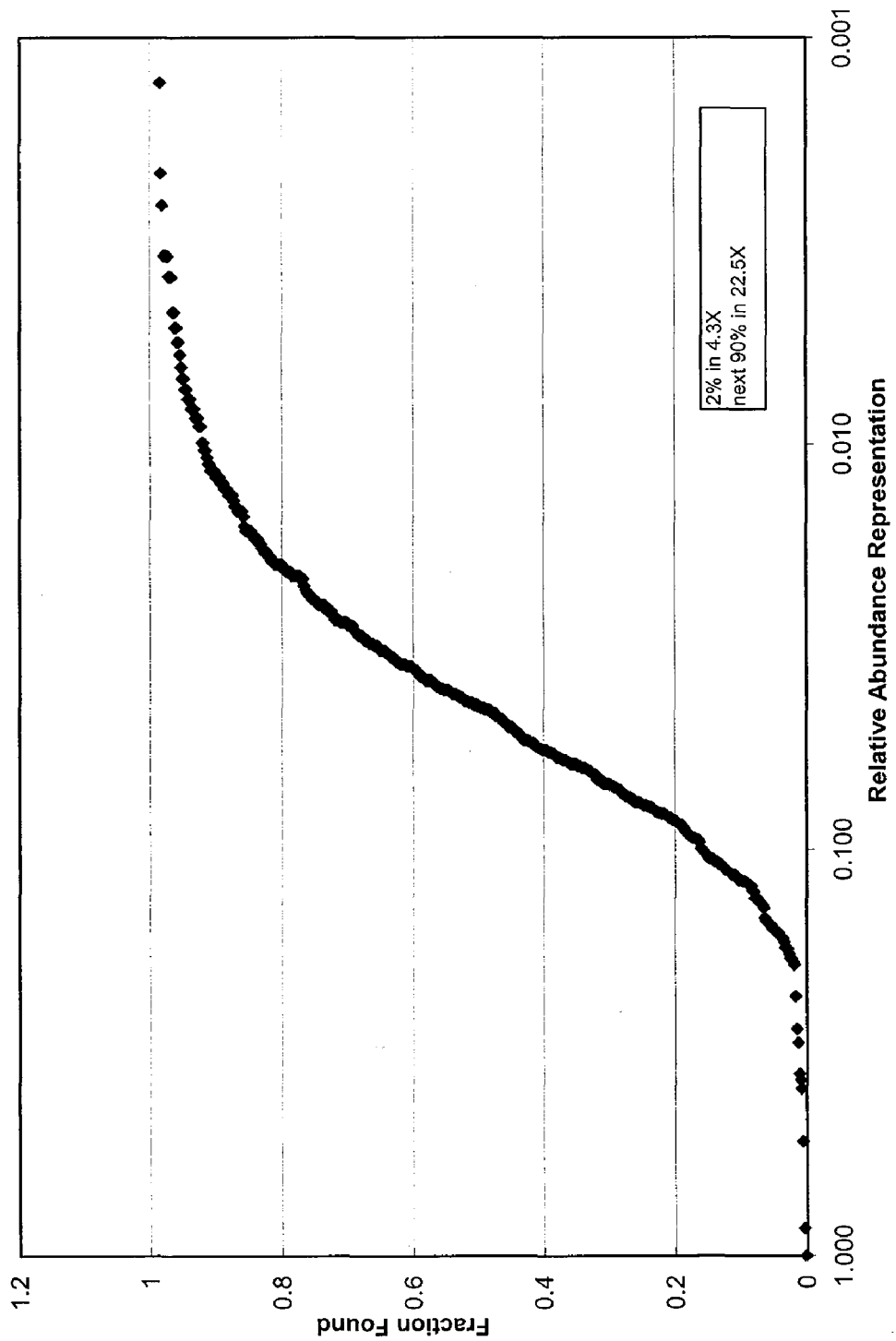
FIG. 2 provides results of the study described in the Example. The graph shows the relative abundance of the extracted targets.
Figure 3:
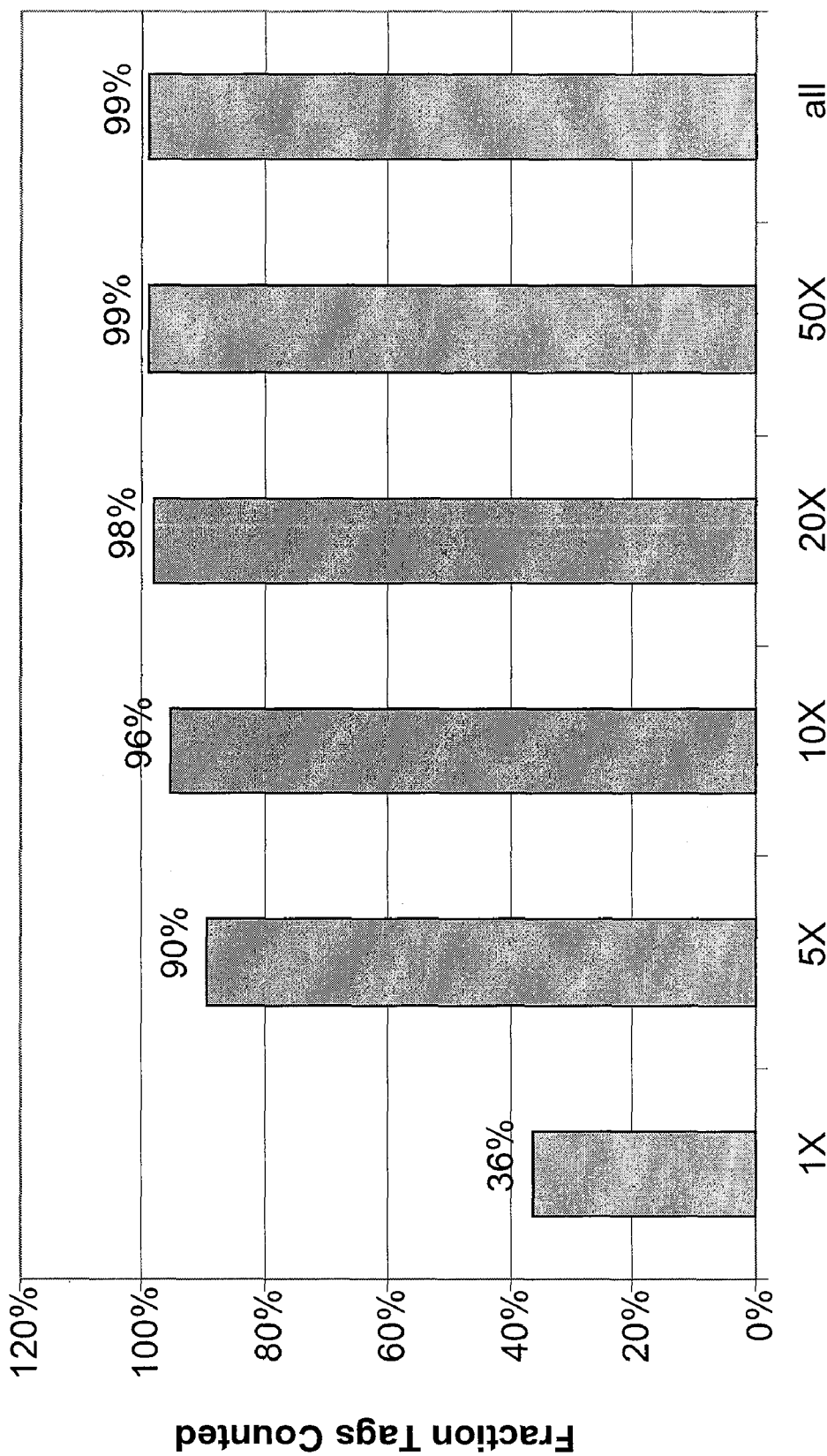
FIG. 3 provides calculated sequencing depth required to "cover" the amplicon pool used in the Example.

FIGS. 1-3 provides results of a representative study performed substantially as described above. The plot in FIG. 1 is the number of amplicons detected vs. probes identity as numbered from 1 to 518. There is no significance to the order of the probes. Results are shown in FIG. 2 expressed as relative abundance of extracted targets. 89,000 target probes were found. Plotted is the abundance of the 518 targets relative to the most abundant, normalized to 1.0 for this most abundant target. For example, targets plotted at 0.01 are 1% as abundant as the most abundant target. In an ideal process, this plot would be a nearly vertical line, all probes present at the same number.

A calculated sequencing depth required to "cover" the amplicon pool is represented in FIG. 3. The calculation was performed as follows: 1) obtain the total length of all amplicons (~110,000 bases); 2) for each of the 110,000 bases sequenced, calculate probability of having sequenced an amplicon. For the first 110,000 bases (referred to as 1× coverage), the statistical estimate is to have sequenced 36% of the amplicons (of note, some of the amplicons at the 36% most abundant probe will be missed and some less abundant amplicons will be seen). For 550,000 bases sequence (5× coverage), one would expect to see at least 1 copy of 90% of the amplicon pool. For 1.1 million bases sequenced (10× coverage), one would expect to see at least 1 copy of 96% of the amplicons present. In practice, the 10× coverage is typically sufficient. A 50× coverage would provide at least 1 copy of 99% of the amplicons.

All publications, patents, patent applications, and biological sequences cited in this disclosure are incorporated by reference in their entirety.

The invention claimed is:

1. A method of equalizing amounts of nucleic acid targets in a sample, the method comprising:
    a) contacting a plurality of probes with a sample comprising a plurality of targets;
    b) capturing the plurality of nucleic acid targets with the plurality of probes;
    c) optionally, amplifying the captured targets using the plurality of probes;
    d) determining an initial range of amounts of different captured nucleic acid targets; and
    e) repeating steps a), b), and c) if performed, at starting concentrations of the probes adjusted to reduce said initial range, thereby producing a final sample.

2. The method of claim 1, wherein the step of amplifying the captured targets is required.

3. The method of claim 1, wherein the targets are amplified by multiplex PCR.

4. The method of claim 1, further comprising f) analyzing the targets obtained in the final sample.

5. The method of claim 4, wherein the targets are analyzed by sequencing.

6. The method of claim 5, wherein the sequencing is sequencing by synthesis or ligation.

7. The method of claim 6, wherein the sequencing by synthesis is performed at a single molecule resolution.

8. The method of claim 1, wherein the capturing step comprises circularizing probes annealed to targets and removing non-circularized nucleic acids.

9. The method of claim 1, wherein the range of representation levels is reduced by at least two-fold.

10. The method of claim 1, wherein the initial range of representation levels is greater than 100× and/or the reduced range of representation levels is less than 50×.

11. The method of claim 1, wherein the starting concentrations of at least five probes are adjusted at least two-fold up or down.

12. A method equalizing amounts of nucleic acid targets, the method comprising:
    a) introducing a plurality of probes to a sample comprising a plurality of targets;
    b) capturing the plurality of nucleic acid targets with the plurality of probes;
    c) optionally, amplifying the captured targets using the plurality of probes;
    d) determining an initial range of amounts of the captured nucleic acid targets;
    e) selecting two or more subsets of targets/probes so that each of the subsets contains targets of a range of amounts that is reduced relative to the initial range; and
    f) repeating steps a), b), and c) if performed, using separate samples so that each sample contains only targets/probes of different selected subsets.

13. The method of claim 12, wherein the method further comprises g) combining the samples produced in step f) or portions thereof to produce a final sample.

14. The method of claim 12, wherein the step of amplifying the captured targets is required.

15. The method of claim 12, wherein the targets are amplified by multiplex PCR.

16. The method of claim 15, wherein in two or more multiplex amplification reactions at least five targets are amplified in each.

17. The method of claim 12, further comprising h) analyzing targets in the combined sample.

18. The method of claim 17, wherein the targets are analyzed by sequencing.

19. The method of claim 18, wherein the sequencing is sequencing by synthesis or ligation.

20. The method of claim 19, wherein the sequencing by synthesis is performed at a single molecule resolution.

21. The method of claim 12, wherein the capturing step comprises circularizing probes annealed to respective targets and removing non-circularized nucleic acids.

22. The method of claim 12, wherein the range of representation levels is reduced by at least two-fold.

23. The method of claim 12, wherein the initial range of representation levels is greater than 100× and/or the reduced range of representation levels is less than 50×.

24. The method of claim 12, wherein five or more subsets of probes are selected.

25. The method of claim 1, wherein two or more subsets of probes comprise at least five probes each.

* * * * *